(12) United States Patent
Gonzales et al.

(10) Patent No.: US 11,219,687 B1
(45) Date of Patent: Jan. 11, 2022

(54) SCORPION REPEL SURFACE TREATMENTS AND METHOD FOR SAME

(71) Applicants: Tony Gonzales, Chandler, AZ (US); Aaron Gonzales, Gilbert, AZ (US)

(72) Inventors: Tony Gonzales, Chandler, AZ (US); Aaron Gonzales, Gilbert, AZ (US)

(73) Assignee: 95 Applications, L.L.C., Chandler, AZ (US)

( * ) Notice: Subject to any disclaimer, the term of this patent is extended or adjusted under 35 U.S.C. 154(b) by 67 days.

(21) Appl. No.: 16/709,371

(22) Filed: Dec. 10, 2019

Related U.S. Application Data

(63) Continuation of application No. 16/456,464, filed on Jun. 28, 2019, now abandoned.
(Continued)

(51) Int. Cl.
| | |
|---|---|
| *A01K 3/00* | (2006.01) |
| *A61K 45/06* | (2006.01) |
| *A61K 36/738* | (2006.01) |
| *A61K 36/61* | (2006.01) |
| *A61K 36/28* | (2006.01) |
| *A61K 36/185* | (2006.01) |
| *A61K 36/752* | (2006.01) |
| *A61K 8/891* | (2006.01) |
| *A61Q 19/00* | (2006.01) |

(Continued)

(52) U.S. Cl.
CPC .............. *A61K 45/06* (2013.01); *A61K 8/585* (2013.01); *A61K 8/891* (2013.01); *A61K 8/922* (2013.01); *A61K 36/185* (2013.01); *A61K 36/28* (2013.01); *A61K 36/61* (2013.01); *A61K 36/738* (2013.01); *A61K 36/752* (2013.01); *A61K 47/24* (2013.01); *A61Q 19/00* (2013.01); *A61Q 17/04* (2013.01); *A61Q 19/08* (2013.01)

(58) Field of Classification Search
None
See application file for complete search history.

(56) References Cited

U.S. PATENT DOCUMENTS

| | | | | |
|---|---|---|---|---|
| 3,236,015 | A * | 2/1966 | Rubenstein | E04C 2/04 52/309.3 |
| 4,923,698 | A ‡ | 5/1990 | Rodero | A01N 25/06 424/40 |

(Continued)

OTHER PUBLICATIONS

Slippery paints: Eco-friendly coatings that cause ants to slip, Feat et al., Progress in Organic Coatings 135 (2019), pp. 331-344.

*Primary Examiner* — Basil S Katcheves
(74) *Attorney, Agent, or Firm* — Howard & Howard Attorneys PLLC

(57) ABSTRACT

A system and method of applying a slick surface, such as silicone epoxy, is applied on a vertical wall (on or around the perimeter of a structure), as a means of preventing (bark) scorpions (or other insects/arachnids) from climbing up walls. The system is intended, in part, to keep the Arizona bark scorpions out of homes. Vertical surface areas around the home are treated with a material such as silicone. A clear silicone epoxy, that when dry, prevents scorpions from climbing vertically up into a home or structure. This non-toxic epoxy is applied to the base of a home, including door thresholds, steps or other parts of a home which makes contact with the ground. The epoxy is applied to the area by sprayer.

18 Claims, 6 Drawing Sheets

Related U.S. Application Data

(60) Provisional application No. 62/691,519, filed on Jun. 28, 2018.

(51) Int. Cl.
| | | |
|---|---|---|
| *A61K 8/58* | (2006.01) | |
| *A61K 47/24* | (2006.01) | |
| *A61K 8/92* | (2006.01) | |
| A61Q 17/04 | (2006.01) | |
| A61Q 19/08 | (2006.01) | |

(56) References Cited

U.S. PATENT DOCUMENTS

| | | | | |
|---|---|---|---|---|
| 5,392,559 | A | * | 2/1995 | Long .............. A01G 13/105 43/108 |
| 5,561,941 | A | ‡ | 10/1996 | Long .............. A01G 13/105 43/108 |
| 5,985,304 | A | * | 11/1999 | Van Voris .......... A01N 25/12 424/403 |
| 6,205,718 | B1 | * | 3/2001 | Murphy ............. A01M 1/14 43/124 |
| 6,223,463 | B1 | * | 5/2001 | Carlson ............ A01G 13/105 43/108 |
| 7,748,161 | B1 | * | 7/2010 | Jordan, Jr. ......... A01M 1/245 43/132.1 |
| 8,256,044 | B1 | ‡ | 9/2012 | Park ................ A47C 29/006 5/414 |
| 8,359,784 | B2 | ‡ | 1/2013 | Sommer ............. A01N 53/00 43/132 |
| 9,253,973 | B2 | ‡ | 2/2016 | McKnight .......... A01M 1/103 |
| 9,353,646 | B2 | ‡ | 5/2016 | Aizenberg .......... A61L 15/34 |
| 2008/0295446 | A1 | * | 12/2008 | Kennedy ............ E04B 1/72 52/741.3 |
| 2009/0298902 | A1 | * | 12/2009 | Taranta ............. A01N 25/10 514/407 |
| 2012/0159874 | A1 | ‡ | 6/2012 | Harrington ........ A01M 29/34 52/101 |
| 2015/0305318 | A1 | ‡ | 10/2015 | Moriarty ........... F15B 15/18 43/113 |

\* cited by examiner

‡ imported from a related application

SCORPION REPEL SURFACE TREATMENTS AND METHOD FOR SAME

CROSS REFERENCE TO RELATED APPLICATIONS

This application is a continuation of U.S. patent application Ser. No. 16/456,464, filed Jun. 28, 2019, which claims priority to and the benefits of U.S. Provisional Patent Application No. 62/691,519, filed Jun. 28, 2018, the contents of which are incorporated herein by reference.

BACKGROUND OF THE INVENTION

1. Field of the Invention

The present invention relates generally to barriers to prevent passage of arthropods, and more particularly to a new and improved barrier and a method to bar the passage of scorpions across a surface of a structure.

2. Description of Related Prior Art

Many insects, like houseflies, are able to walk on and cling to seemingly smooth surfaces—including glass doors and windows. They accomplish this not by using suction or adhesives, but rather, they use a large number of tiny bristles or hairs on the bottom surface of their feet or appendages. Surfaces that appear perfectly smooth, like glass, actually have many microscopic bump and fissures, which serve as footholds for the tiny hairs. This is not the case of scorpions. Although scorpions have sensory hairs (or tarsal hairs) on their appendages, they do not use them for migration or climbing. Scorpions rely upon their "ungues" or "tarsal claws" and a shorter claw or "dactyl" to climb surfaces. Unlike other insects, these claws are too large to use the footholds on smooth surfaces.

The use of surface modifications is known in the art as a means of deterring and preventing passage of certain insects and other pests. For instance, scents may be used to repel certain mammals, diatomaceous earth has been used to injure passing arthropods, neurotoxins are used as repellents, and surface coating treatments have been applied to deter insects. The special nature of larger arachnids, and especially scorpions, requires a suitable deterrent.

Smooth surfaces have been known in the art for deterring termites, ants, and other insects. Such surfaces must be prepared in a manner to interact with, and deflect, the insect hairs, and otherwise prevent adhesion and motility. However, such surface treatments may fail to stop or slow a scorpion due to the difference in their mobility—wherein scorpions rely on ungue-motion.

Alternatives for pest control and scorpion deterrence have involved capture methods that, while useful, may require periodic inspection, replacement, and disposal. These systems further fail by requiring the distasteful interaction with a live (or even dead) scorpion. Hazards may arise with the disposal or moving of a live scorpion.

It is therefore a primary object of the present invention to provide a barrier for the deterrence of pests.

It is another object of the present invention to create a barrier that prevents scorpions from climbing past.

It is yet another object of the present invention to treat surfaces for the deterrence of pests.

These and other objects of the present invention will become apparent to those skilled in the art as the description thereof proceeds.

SUMMARY OF THE INVENTION

The present invention is directed to a barrier system for the prevention of scaling scorpions across a flat, preferably vertical, surface with a thin layer of dry silicone epoxy applied to the surface. The thin layer is preferably applied on an exposed foundation, and preferably outlines a stripe circumscribing the structure. Additional stripes, such as a second stripe of pesticide, may be applied along, adjacent, above or below the first stripe of silicone epoxy. The thin layer should be at least three inches wide, if not 3.5 inches or wider. The thin layer DFT should be at least 3.4 mil thick.

The present invention also includes a method of applying a barrier to a vertical surface to prevent the passage of scorpions and other animals up a wall by preparing a substantially vertical surface for application of a silicone epoxy, and then applying a first spray layer of silicone epoxy to the surface, the first spray layer forming a stripe that is at least one inch wide, and more preferably at least three inches wide, or most preferably 3.5 inches wide or wider. The application should achieve a DFT thickness of the silicone epoxy at least 2 mil, and most preferably at least 3.4 mil. Multiple horizontal strokes may be required to achieve preferred DFT. Additionally, a second stripe of pesticide may be applied next to, below or above the first spray layer of silicone epoxy.

BRIEF DESCRIPTION OF THE DRAWINGS

The present invention will be described with greater specificity and clarity with reference to the following drawings, in which.

DETAILED DESCRIPTION OF THE PREFERRED EMBODIMENTS

One purpose of the present invention is to achieve a physical barrier on a vertical surface, such as a wall, flashing or otherwise, to prevent scorpions from climbing up surface. The resultant layer of silicone epoxy provides a solid slick surface that cannot be scaled by hook-based motility found in scorpions. Given the nature of applied silicone epoxy, the barrier may not work well to deter other arthropods such as ants or spiders, or other larger animals such as lizards, rodents, etc. The layer is preferably sprayed the entire circumference of the house, in a continuous ring so as to prevent scaling and crawling of scorpions.

Silicone epoxy is preferably a resin blend featuring a silicone-alkyd base fortified with mono-epoxy resins producing a finish that is both hard and flexible at the same time. The finish is less likely to fade, lose its gloss, peel or crack even in high altitude, high UV environments. The silicone epoxy should adhere to almost any surface and self-levels. The silicone epoxy should offer good resistance to chemicals, and weather, and should be impact resistant to 500 psi and is heat resistant to 400 F.

Silicone epoxy may be dew point sensitive. High humidity may slow dry times and could cause it to have improper surface/friction qualities. A preferred silicone epoxy is catalyzed by oxygen, and not chemically catalyzed as are many typical epoxies known in the art. The applied film may be soft at first. One can expect to see approximately 70% of the total cure within one week when applied at two mils maximum thickness. The film will continue its natural curing process for 2-3 weeks, depending on film thickness, air movement, temperature, humidity, and color. Baking the film is expected to have no beneficial results and it is recommended not to add heat to the curing process. After two days the finish will still mark or scratch easily.

Figure 1:
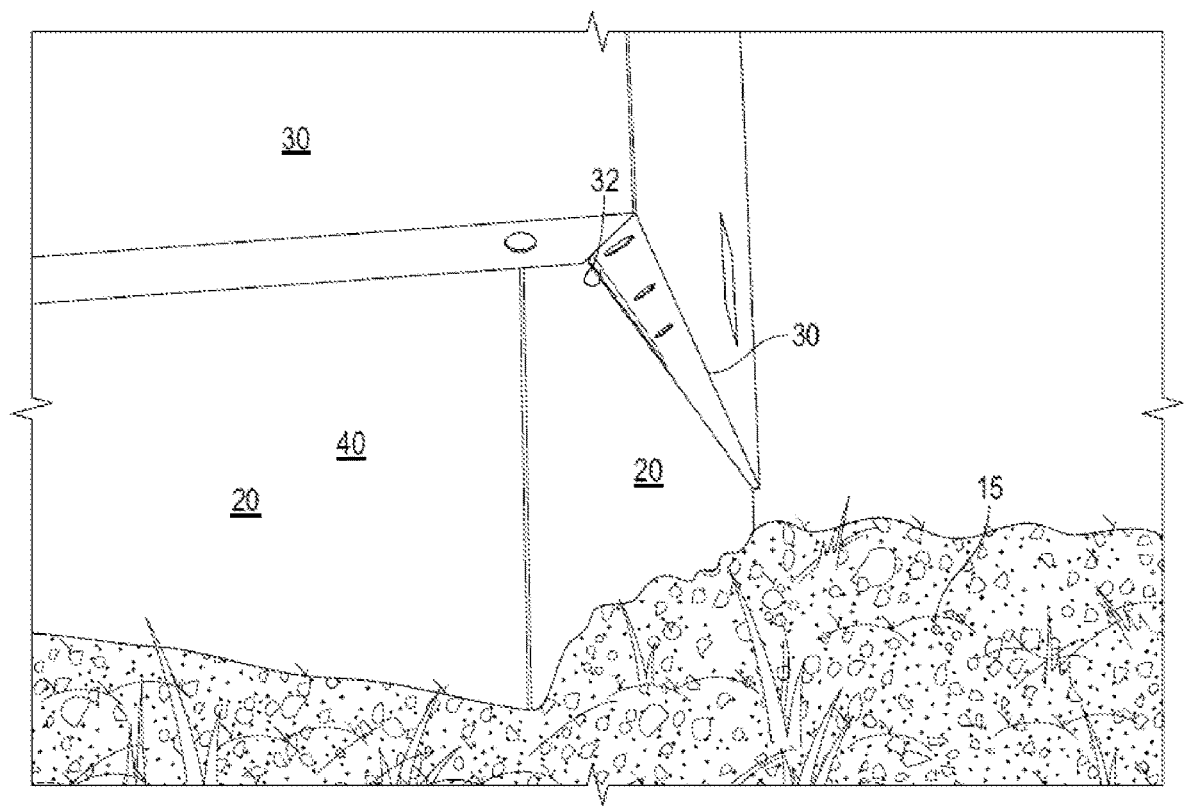
FIG. 1 illustrates a structure with exposed flashing applied with a coating of the present invention.

As shown in FIG. 1, silicone epoxy may be applied to exposed foundation in typical masonry/stucco homes as are often commonly built in the twenty-first century. An exposed foundation 20 may emerge over the ground level 15 and expose approximately two to six inches of mostly vertical foundation 20, or flashing. Flashing may be exposed concrete, or other treatments, such as metal plating, paint, etc. The ground 15 is often set back at two- or four-degree slope to prevent liquid build up against the foundation 20 by allowing drainage away from the building structure. Additionally, the building 30 sits upon the foundation 20 and is set above the ground level to prevent flooding, but also to provide a minor barrier to crawling pests. However, it is known that the concrete often used for foundations provides a suitable surface to allow crawling insects and other pests, including scorpions, to access the building through recesses 32, holes, cracks, etc. planned or otherwise imperfections that inevitably occur in the building. While neurotoxins and other pesticides may be applied around the house, or on the foundation, the present invention provides a physical barrier specially formulated and structured to prevent crawling of scorpions by ungues. A thin layer 40 acts as a permanent flashing against the foundation 20.

Silicone Epoxy resin blend may be applied to the exposed foundation section. Silicone may be combined with epoxy produces a finish that is both hard and flexible at the same time. The self-leveling finish is remarkably glossy and smooth. A standard paint thinner may be used to thin out the silicone epoxy. Thinners may be self-leveling and/or may include standard products such as acetone, or other thinning agents known in the art. Preferably the silicone epoxy is thinned by at least 10% and more preferably 20-30%. Mineral spirits may also be used to clean and/or thin out the silicone epoxy.

The silicone epoxy is preferably applied by a spray to a vertical surface. The term vertical surface may include an absolute vertical surface, or one two degrees, or as much as four degrees off of true vertical (referred to herein as substantially vertical). As a purpose is to combine the force of gravity with the lack of climbing holds, any rising surface may be used, including an angle up to thirty or even forty-five degrees off of vertical. Spray may be powered by an air compressor attached to a high velocity/low pressure sprayer (HVLP) (such as a gravity-feed spray gun). The air compressor is preferably set at thirty psi. The low pressure is often required to limit or prevent splash and bouncing of silicone epoxy as it is applied, and is often necessary for a complete coverage as the self-leveling occurs to provide a proper and complete coverage to the surface. Gravity guns are preferred as they include more clearance below the spray head.

The site is preferably prepared for application of spray coating by removal of vegetation and large objects to a distance from structure by at least two feet. Further, Surface preparation is critical. Previously painted surfaces must be thoroughly cleaned and free of residues, oily film, and loose paint chips. Wire brushing and washing the surface are also preferred prior to application. Silicone epoxy is preferably mixed with a thinner immediately prior to application, the thinning completed on site. Based on circumstances and conditions, the silicone epoxy must be appropriately thinned to an appropriate viscosity to result in proper application (spray droplets, speed, viscosity, coverage, self-leveling). Humidity level of the environment should be checked and appropriately applied to the thinning control as is known in the art. The prepared silicone epoxy blend is then preferably fed into a gravity feed spray gun. Volume, fluid control knob, is typically set at maximum to ensure consistency and product flow.

The spray is designed for application in a manner thinner than typical paint. Maximum wet film thickness (WFT) is preferably only 2 mils on a per coat basis. The recommended dry film thickness (DFT) is 3.4 mils, comprising a thin layer. When applied too thickly the lower layers will be deprived of oxygen which may result in extended dry and cure times, discoloration or a failed application. The DFT should be at least 3 mils, and does not need to be more than 6 mils to ensure leveled surface when prepared properly. More erratically scarred surfaces may require a thicker coat. Multiple coats are applied (if needed) to achieve the recommended DFT. If it runs or sags it has been applied too thickly. Adhere to the maximum recommended WFT. Test applications may be used to prevent many problems. The final DFT is measured after self-leveling and drying. Dilution of the silicone epoxy is required in virtually all applications, but may be left out circumstances requiring.

It is preferable that the width (or commonly referred to as height when viewing a horizontal stripe) of the barrier stripe is at least wide enough to prevent contemplated creatures (i.e. bark scorpions, etc.) from passing over the stripe in a single bound. The stripe is preferably at least one inch wide, and more preferably at least three inches wide. Preferably, the stripe circumscribes the building structure, such as following the path around a house foundation. Often walls or other (semi-)permanent features will obstruct the continuity of the circumferential stripe that cannot be moved easily when applying the stripe coating. In order to work around such obstacles, a gap may be present, or the stripe may have to deviate from the height of application to follow the contour of the obstacle. As an alternative, the stripe may be applied not only around the structure, but in a continuous loop around the structure and all adjoining surfaces. It is preferably that the stripe be applied as a continuous barrier around the structure. As a uniform height may not always work in every case/structure, the stripe may bend, curve, or turn, when circumscribing the structure (base).

Figure 6:
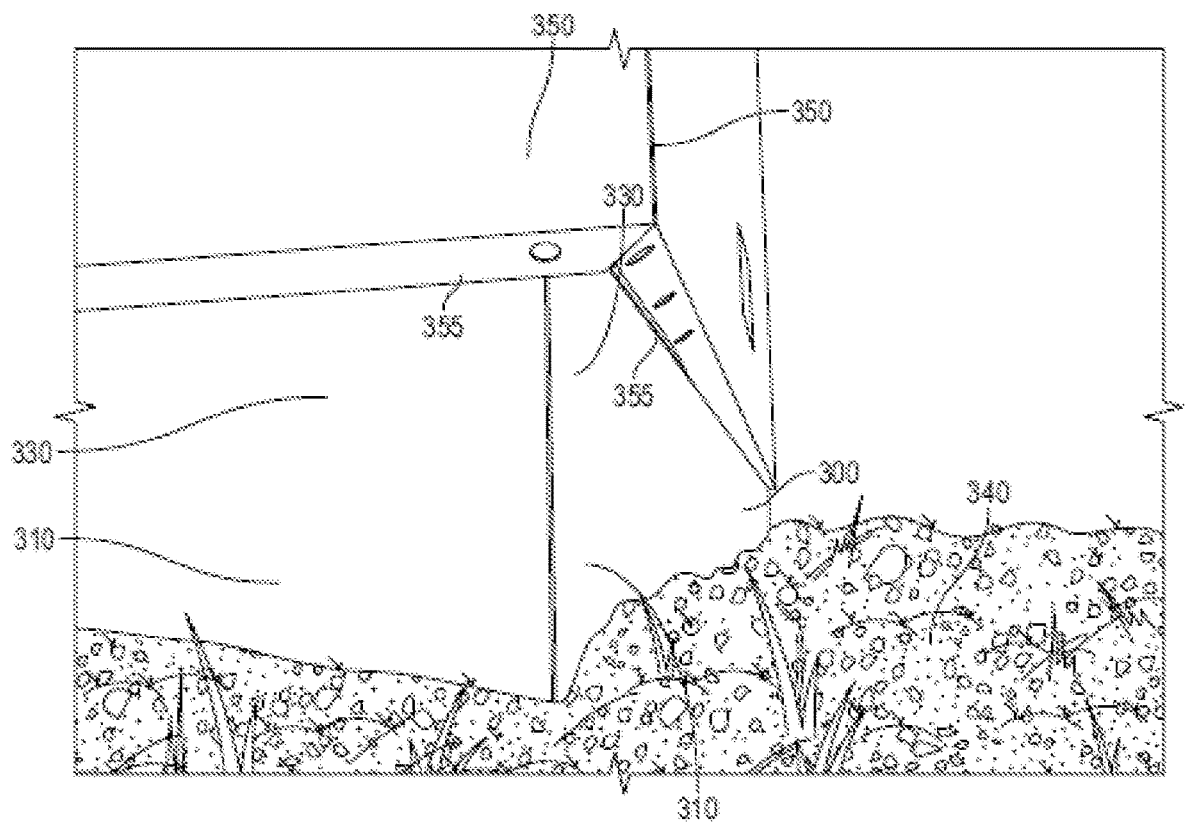
FIG. 6 illustrates a structure with exposed flashing applied with an alternative embodiment of the present invention.

As the silicone epoxy stripe barrier suffers a potential weakness against other creatures, additional barriers may be used in conjunction with the stripe. For instance, the ground below the stripe may be treated with a chemical (Imidacloprid, lemon oil, etc.) or powder (e.g. diatomaceous earth, cinnamon, etc.) to provide a barrier to other creatures. Additionally a second stripe may be painted, coated, sprayed, or otherwise applied in parallel with the stripe or otherwise (e.g. on walls and around doors, etc.) around the structure. In a preferred case, a four inch exposed foundation flashing will be coated with a three-inch-wide silicone epoxy stripe next to (and possibly adjacent, and possibly overlapping) a pesticide shield/barrier stripe (e.g. one inch in width). It is contemplated that any treatments will be conducted on cleaned surfaces, and if possible, the silicone epoxy treatment will either be applied first, or if applied earlier, will be wiped and cleaned after application of other treatments. For instance, as seen in FIG. 6, silicone epoxy barrier 310 is applied to foundation 300 in approximately a three-inch-wide (tall) stripe around corner 302. Additional pesticide treatment barrier 330 is applied as a one-inch-wide stripe there above. A ground treatment barrier 340 may also be applied to the surface. Where a 3.5 inch or wider silicone epoxy stripe is preferred, pesticide barrier may also be applied to underside 355 of jutted building corner wall 350.

The curing process should be allowed to be completed naturally and air thy. We recommend the fingernail mark test to determine hardness. When it passes the fingernail mark test you know it has cured hard enough to enter full duty service.

The application of a silicone epoxy, such as that provided by Top Secret Coatings Inc. of New Jersey in the TS-100 Silicone Epoxy as a one-part epoxy industrial marine paint, is indicated. Protective coating that is easier to use, more durable, and longer lasting than traditional catalyst-cured two component epoxy or urethane resin blend featuring a silicone-alkyd base fortified with our exclusive mono-epoxy resins producing a finish that is both hard and flexible at the same time. The finish is less likely to fade, lose its gloss, peel or crack even in high altitude, high UV environments. The silicone epoxy adheres to almost anything and self-levels high-gloss, high-performance coating that features the toughness of epoxy, and the weather-ability and durability of silicone alkyd. It is a fully submersible waterproof barrier coating resistant to many alkalis chemicals and staining agents. It is self-leveling and is acceptable in higher heat applications. It resists chipping, peeling and cracking on properly-prepared substrates and is UV stable Surface preparation is critical. Previously painted surfaces must be thoroughly cleaned and free of residues, oily film, and loose paint chips. Wire brush before painting. Areas where all of the old coating has been removed must be spot primed before applying finish coat. Surface preparation is critical. Previously painted surfaces must be thoroughly cleaned and free of residues, oily film, and loose paint chips. Wire brush before painting. Areas where all of the old coating has been removed must be spot primed before applying finish coat.

Figure 2:
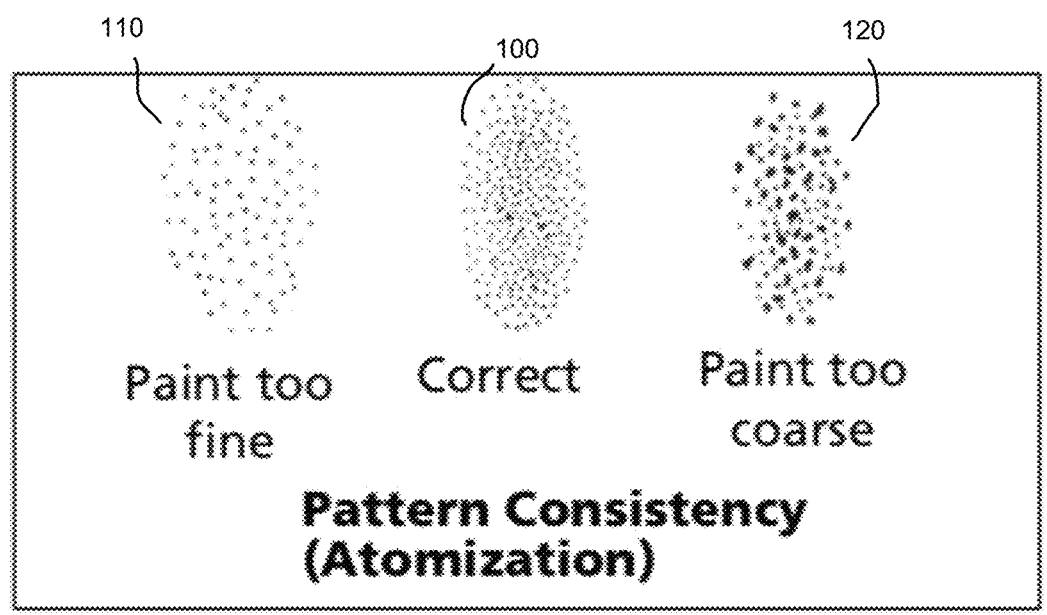
FIG. 2 illustrates various spray patterns on a surface.

As shown in FIG. 2, an appropriate spray pattern of the silicone epoxy should be applied to the surface. Fine patterns 110 will fail to provide adequate coverage and may lead to untreated surface, while coarse patterns 120 may lead to a lumpy or inconsistent surface that may provide a foothold. Only a proper correct pattern 100 executed under appropriate pressure and will result in the expected level surface treatment necessary to prevent passage of crawling scorpions and the like.

Figure 3:
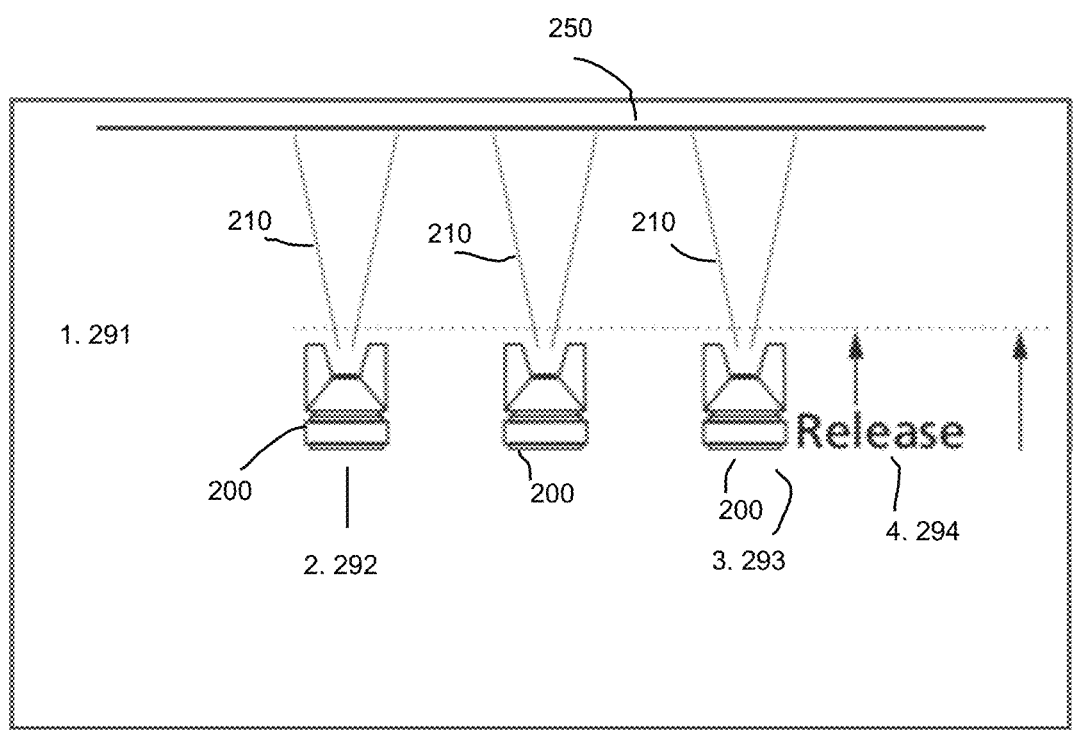
FIG. 3 illustrates a top view of the spray application process.
Figure 4:
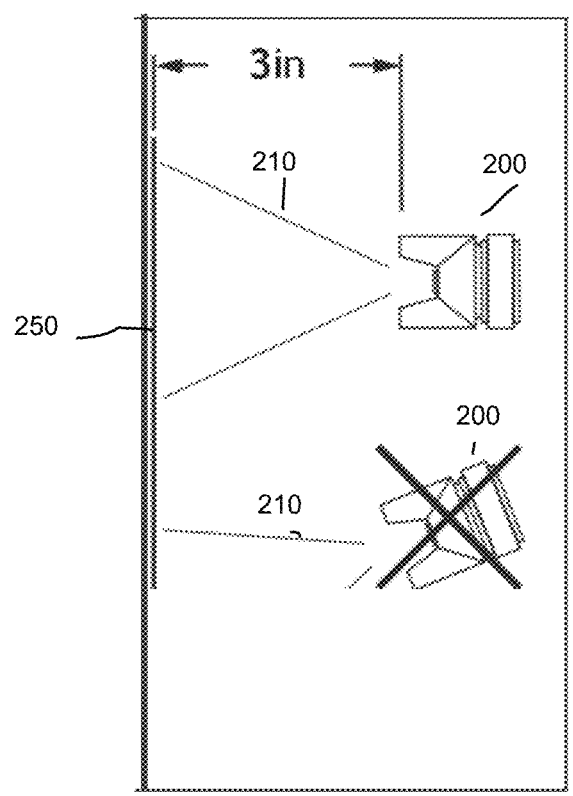
FIG. 4 illustrates a top view of an alternative spray application process.

As seen in FIGS. 3 and 4, appropriate spray distance and angle should be approximately three inches from the surface and angle deviation from perpendicular should be minimized. Spray head 200 emits spray 210 to treat surface 250. Spray head 200 should be aligned to provide a tall emission (up/down with occluded sides (left/right) as is known in the art. A proper method of treating the surface includes a stroke. First the stroke is started by initiating horizontal movement 291, then the trigger is pulled initiating the spray 292, the movement horizontally should be consistent in speed. While still moving horizontally and maintaining proper distance (approx. 3 inches) the trigger is released 293. Movement continues during the release 293. Movement is then later ended and the stroke is completed 294. Distance may be modified as need depending on conditions, temperature, humidity, wind, surface features, and viscosity of fluid. To modify the height of application, it is preferable to begin a stroke at a different height. Alternatively, up/down motion may be applied. Preferably, for up/down motion, the spray head is adjusted and rotated ninety-degrees to provide spray pattern.

The spray should cover preferably 3.5 inches in vertical height along the vertical surface. It is contemplated that the creature will be dissuaded from attempted climb. See attached scorpion and arachnid leg profile. The barrier is intended to prevent climbing by hook style legs, rather than traditional, hair grip, and other motility shown by ants, geckos, etc. Coverage of 3.5 inches of a 4" flashing, or approximately 80% of the vertical climb is preferred. Application is preferably close to the ground on a mostly smooth surface. Application is preferable on exposed foundation, or flashing, seen in many stucco-finished homes. When flashing is 6-8", two to three passes (one above the other) may be necessary.

Figure 5:
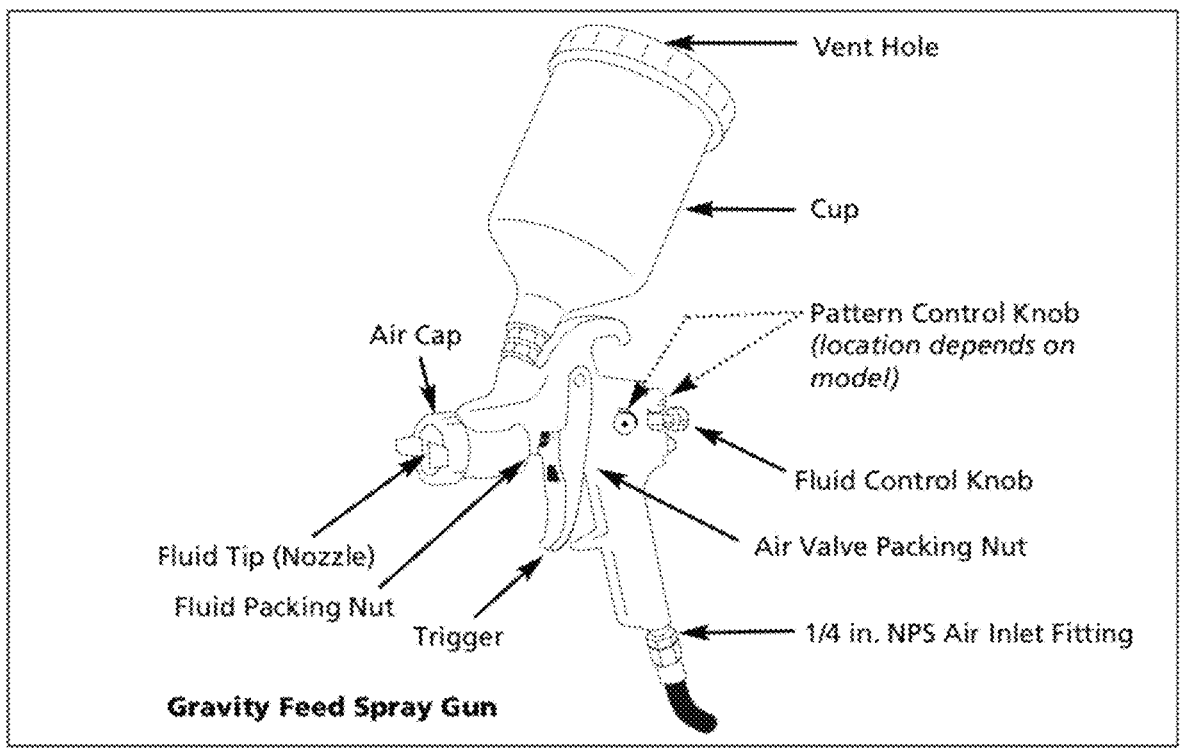
FIG. 5 illustrates a preferred gravity spray gun as an applicator for an embodiment of the present invention.

Essential tools as set forth in FIG. 5 will be readily understood by one having ordinary skill in the art. A wire brush and sponge brush may be used to prepare the surface for treatment. Masking tape can be used to protect the structure and ground, and otherwise prevent inadvertent coating of surfaces meant to be kept clean. In addition to essential tools, other equipment may be utilized in the treatment process. A compressor is powered via an extension cord (preferably retractable to prevent tripping an interference with spray). Hoses provide fluid connections to the compressor, and mixture, and other fluids. The spray gun may be set up to mix the thinner solution (such as mineral spirits, etc.) with the silicone epoxy in the gun prior to spray head release. Brushes can be used to prepare surfaces, long with dish soap plastic covering around treated area and tape. Application user should use protective gear such as a body suit, goggles, and shoe coverings. A pump sprayer may be used with a soap solution, or other cleaning solution (including plain water) to prepare and/or clean-up site.

In preparing for the treatment, one may use a degreaser such as TSP to remove stubborn oil or grease. Rinse thoroughly. Power-washing, sanding or blasting is recommended but not required on clean well prepared surfaces. Next wash surface with an etching cleaner. Concrete may continue to leach lime even after it has cured so etch before proceeding. Allow to dry thoroughly and wait at least 48 hours or test for moisture to ensure dryness. One test may include taping edges of a clear plastic sheet to the surface and waiting a few hours. If moisture is evident it is too wet. Wait until there is no sign of moisture before proceeding.

In some applications, multiple coatings may be used. Applying a first coat of silicone epoxy serves as primer coat. Stir thoroughly then dilute 25% with thinner. Silicone epoxy is applied evenly avoiding heavy build up. In some cases multiple applications over multiple days is needed. When doing so, allow first coat to dry 12-48 hours before recoating. A second coat may be applied, and if so, should be applied evenly avoiding ponding and heavy build up. Alternatively, the second, potentially third, fourth and more coats may be applied on the same day, including after a few minutes, hours, or immediately after the stroke.

We claim:
1. A barrier system comprising:
   a. a substantially vertical, exterior surface of a home; and
   b. a layer of cured silicone epoxy disposed on said substantially vertical, exterior surface;
   wherein said layer has a smooth surface configured to prevent scorpions from reaching an upper portion of said substantially vertical, exterior surface of a home located above said layer of cured silicone epoxy.

2. The barrier system of claim 1, wherein said substantially vertical, exterior surface is an exposed foundation.

3. The barrier system of claim 1, wherein said layer comprises a stripe circumscribing said home.

4. The barrier system of claim 3 further comprising a second stripe of a pesticide applied to the surface along the stripe.

5. The barrier system of claim 1, wherein said layer is at least three inches wide.

6. The barrier system of claim 1, wherein said layer has a dried film thickness (DFT) of at least 3.4 mil thick.

7. A method of forming a barrier system to prevent scorpions from reaching an upper portion of a substantially vertical, exterior surface of a home, said method comprising the steps of:
   a. preparing the substantially vertical, exterior surface for application of a silicone epoxy;
   b. spray applying a layer of silicone epoxy to the surface to form a stripe that is at least one inch wide; and
   c. allowing the layer of silicone epoxy to cure and form the barrier system;
   wherein the layer of silicone epoxy has a smooth surface configured to prevent scorpions from reaching an upper portion of the substantially vertical, exterior surface of a home located above said layer of cured silicone epoxy.

8. The method of claim 7 wherein spray applying achieves a dried film thickness (DFT) of the silicone epoxy at least 3.4 mil.

9. The method of claim 8 wherein spray applying includes multiple horizontal strokes.

10. The method of claim 8 wherein the silicone epoxy is a blend of a silicone-alkyd and mono-epoxy resins.

11. The method of claim 8 wherein the spray applied layer of silicone epoxy self-levels during curing to produce the smooth surface.

12. The method of claim 7 further comprising the step of applying a stripe of pesticide above the layer.

13. A barrier system comprising:
   a. a substantially vertical, exterior surface of a home; and
   b. a layer of silicone epoxy disposed on said substantially vertical, exterior surface;
   wherein said layer has a smooth surface configured to prevent scorpions from reaching an upper portion of said substantially vertical, exterior surface of a home located above said layer of cured silicone epoxy; and
   wherein said silicone epoxy is formed by curing a blend of a silicone-alkyd and mono-epoxy resins in the presence of an oxygen catalyst.

14. The barrier system of claim 13, wherein said substantially vertical, exterior surface is an exposed foundation.

15. The barrier system of claim 13, wherein said layer comprises a stripe circumscribing said home.

16. The barrier system of claim 15 further comprising a second stripe of a pesticide applied to the surface along the stripe.

17. The barrier system of claim 13, wherein said layer is at least three inches wide.

18. The barrier system of claim 13, wherein said layer has a dried film thickness (DFT) of at least 3.4 mil thick.

* * * * *